United States Patent [19]

Campbell

[11] Patent Number: 5,053,049
[45] Date of Patent: * Oct. 1, 1991

[54] FLEXIBLE PROSTHESES OF PREDETERMINED SHAPES AND PROCESS FOR MAKING SAME

[75] Inventor: Todd D. Campbell, Corona, Calif.

[73] Assignee: Baxter International, Deerfield, Ill.

[ * ] Notice: The portion of the term of this patent subsequent to Jul. 7, 2006 has been disclaimed.

[21] Appl. No.: 738,760

[22] Filed: May 29, 1985

[51] Int. Cl.⁵ .............................................. A61F 2/28
[52] U.S. Cl. ...................................... 623/16; 623/66; 623/18
[58] Field of Search ................... 623/1, 11, 16, 18, 66; 128/1 R, 334

[56] References Cited

U.S. PATENT DOCUMENTS

| | | |
|---|---|---|
| 4,120,730 | 10/1978 | Trojer et al. |
| 4,172,128 | 10/1979 | Thiele et al. |
| 4,257,405 | 3/1981 | Colville |
| 4,277,238 | 7/1981 | Kategiri |
| 4,309,488 | 1/1982 | Heide et al. |
| 4,330,891 | 5/1982 | Branemark et al. |
| 4,394,370 | 7/1983 | Jefferies |
| 4,407,793 | 10/1983 | Akimova et al. |
| 4,440,750 | 4/1984 | Glowacki |
| 4,472,840 | 9/1984 | Jefferies |
| 4,485,096 | 11/1984 | Bell |
| 4,485,097 | 11/1984 | Bell |
| 4,597,766 | 7/1986 | Hilal et al. ............................ 623/16 |
| 4,627,853 | 12/1986 | Campbell et al. |
| 4,678,470 | 7/1987 | Nashef et al. ......................... 623/16 |

FOREIGN PATENT DOCUMENTS 2148122A 5/1985 United Kingdom.

OTHER PUBLICATIONS

Gross et al., *Oral Surg.*, vol. 49, No. 1, pp. 21–26, Jan. 1980.
Urist et al., *Proc. Nat'l. Acad. Sci. U.S.A.*, vol. 76, No. 4, pp. 1828–1832, Apr. 1979.
Takagi et al., *Ann. Surg.*, vol. 196, No. 1, pp. 100–109, Jul. 1982.
Gupta et al., *International Orthopaedics*, vol. 6, pp. 79–85, 1982.
Gupta and Tuli, *Acta Orthop. Scand.*, vol. 53, pp. 857–865, 1982.
Narang et al., *J. Oral Maxillofac. Surg. (U.S.)*, vol. 40, No. 3, pp. 133–141, Mar. 1982.
Glowacki et al., *Calcified Tissue International*, vol. 33, pp. 71–76, 1981.
Wittbjer et al., *Scand. J. Plast. Reconstr. Surg.*, vol. 16, pp. 239–244, 1982.

*Primary Examiner*—David J. Isabella
*Attorney, Agent, or Firm*—Rothwell, Figg, Ernst & Kurz

[57] ABSTRACT

Flexible prostheses of predetermined shapes are derived from bone. The process includes machining of a bone segment into the desired shape, demineralization to impart the desired degree of flexibility, and tanning to render the material non-antigenic, biocompatible, and stabilized.

23 Claims, No Drawings

FLEXIBLE PROSTHESES OF PREDETERMINED SHAPES AND PROCESS FOR MAKING SAME

BACKGROUND OF THE INVENTION

Many prostheses and implants are known which are used to replace body parts missing due to injury, disease, or birth defects or to augment existing body parts. The prostheses have been derived from both artificial and natural materials. The materials used for constructing such prostheses must be chosen carefully and/or processed to avoid the problems of antigenicity and bioincompatibility, while still duplicating as closely as possible the natural shape and texture of the body part to be replaced or augmented.

Production of prostheses that are flexible yet duplicate the shape of contoured body parts such as the outer ear has been attempted with limited success. For example, silicone ear implants have been produced, but were found to lack durability and to be prone to tearing. Outer ear prostheses have also been derived from flexible portions of autogenic rib material (taken from the individual for whom the ear prosthesis is being made). Prostheses derived from this costal (rib) material are generally too soft to retain intricate detailed shapes and contours. As a result, the implanted prostheses do not resemble natural human outer ears. The necessity of performing additional surgery (with the accompanying risk of infection, discomfort to the patient, and extra expense) to obtain the rib material is another disadvantage of this procedure.

A need remains for a method of producing prostheses (such as outer ear prostheses) that are flexible yet have predetermined detailed and contoured shapes. These prostheses should be comprised of material which is bio-compatible, non-antigenic, durable enough to resist tearing or rupturing, and capable of being formed into (and retaining) an intricate shape. Additional surgery to obtain starting material (for derivation of the prostheses) from the individual to receive the prosthesis should be avoided.

SUMMARY OF THE INVENTION

In accordance with this invention, flexible or semi-flexible prostheses of predetermined shapes can be derived from bone, which can be machined into any desired size and shape. Selective demineralization of the bone imparts the desired degree of flexibility to the prosthesis without causing loss of the predetermined shape. The bone is treated with a tanning agent to yield a biocompatible, non-antigenic, and stabilized material. The method of this invention is especially useful for production of prostheses used to replace flexible body parts having precise, intricate shapes, such as the outer ear.

DETAILED DESCRIPTION OF THE INVENTION

The present invention is directed to a method of producing a prosthesis or template useful for replacement or reconstruction of flexible cartilagenous body parts, as well as the prostheses or templates so produced. The method may be used to produce spinal column discs or implants for reconstruction of the tip of the nose or for chin augmentation, for example. The method is especially useful for production of flexible implants which desirably have a precise, intricate shape such as outer ear prostheses.

The prostheses are derived from bone, which can be machined into the exact desired prosthesis shape. Selective demineralization of the bone imparts the desired flexibility, and tanning of the bone yields a biocompatible, non-antigenic, and stabilized material. The multi-step process for producing the prostheses of the invention is described below. The term "prosthesis" as used herein includes devices useful not only for replacement of entire body parts but also for replacement of portions thereof or for augmentation of existing parts.

The order of the steps may vary, but the process begins with selection of a bone source from which the desired prosthesis can be derived. Since later treatment with glutaraldehyde renders the bone non-antigenic by cross-linking the proteins, the bone may be taken from a wide variety of xenogenic or allogenic sources, including bovine, ovine, equine, or porcine bone. The bone is advantageously large enough that a prosthesis of the desired dimensions can be machined from it in one piece.

The bone stock is obtained fresh, and the desired section of bone is grossly removed by suitable means such as cutting with a saw, with frequent rinsing of the bone in a fluid such as distilled water or saline to keep it moist and cool (at or below physiological temperatures to prevent denaturation of bone material) during cutting. Preferably, the bone piece is taken from the condylar section of a long bone. Associated connective tissue (tendons, ligaments, and fascia) is removed. In the case of an ear prosthesis, the desired bone piece is a thin bone plate (approximately ¼ to 3/16 inch thick) which may be cut directly from the bone stock or cut from the larger, grossly removed bone piece initially removed from the stock. Optionally, the bone piece may be frozen at this point if further processing is to be delayed.

Any conventional means of machining hard materials, including the use of drills, saws, grinders, carving tools, and the like may be used to obtain the desired final prostheses shape from the bone pieces. For example, a rough outline of the outer circumference of the prosthesis may be drawn on the bone plate, and this section may be cut from the plate using a saw. Guide markings may be made on the bone piece to indicate any depressions, ridges, openings, or other details desired in the final prosthesis.

Optionally, templates having desired shapes and contours (such as those of a human outer ear) may be made from any suitable material (such as metal) in a range of sizes. A cutting tool, drill, or other machining instrument may be inserted into a pantograph and positioned over a bone piece. A pen or similar pointed instrument is also inserted into the pantograph and is moved over the surface of the template, outlining the edges and contours of the template. Movement of the pen over the template causes cutting of the bone piece into the contours being traced on the template. Repeated tracing over an area produces deeper cuts, yielding the desired contours in the bone piece.

In the case of an ear prosthesis a hole must be made at the point at which the prosthesis will be over the ear canal once attached in place. The cavities and contours of a natural ear can be precisely duplicated by the machining process. The two cavities comprising the thinnest parts of a human ear may be duplicated by precise machining to leave a very thin bone layer at the bottom of each cavity. Advantageously, however, holes are machined into the ear prosthesis at these two points. This prevents fracturing of the thin bone layer that would have been at the bottom of each cavity. In addition, when the prosthesis is in place and sandwiched between two flaps of skin, the skin will bridge the holes at the cavity site, thus simulating a natural ear.

Machining of the bone piece produces the final prosthesis shape according to exact pre-determined specifications regarding size, shape and detail. This shaping may be done prior to, rather than during, the implantation surgery.

The shaped bone piece is selectively demineralized to impart to it the desired degree of flexibility. Any suitable demineralizing solution may be used, including but not limited to organic or mineral acids such as HCl and/or a suitable $Ca^{++}$ chelator such as EDTA. Preferably, the demineralizing solution comprises 0.1 to 1N HCl, and most preferably comprises 0.6N HCl. Advantageously, the demineralizing solution also comprises up to 1% EDTA, most preferably 0.1% EDTA. The bone piece is submerged in the solution and the extent of demineralization is monitored by any suitable means, including X-ray analysis. Advantageously, the demineralization process is monitored simply by checking the feel of the prosthesis at regular intervals. When the desired degree of flexibility (usually complete demineralization) is achieved, the prosthesis is rinsed in a non-demineralizing solution such as buffered saline.

The bone piece may be cleaned with an organic solvent, such as with ethanol to defat the material and remove machine oil and debris. The surface cleaning is preferably done by submerging the bone piece in at least one, most preferably several, rinses of room temperature 100% ethanol. The bone piece can then be rinsed well in a saline solution.

Advantageously, the prosthesis is treated to increase the porosity of the matrix. This treatment may be accomplished by extracting the bone piece with an organic solvent (e.g., chloroform, ethanol, chloroform:methanol 1:1), acetone or similar solvents) to remove non-matrix-bound proteins, followed by rinsing in physiological saline to remove the organic solvent. Oils that may have exuded from the bone material are also removed. This porosity-increasing step may also include treatment of the bone piece with a protease such as Pronase ®, collagenase, or hypluronidase (all commercially available). The degree of porosity can be determined visually and confirmed by light or electron microscopy. Optionally, this step may be done before the demineralization step.

The prosthesis is tanned to a degree sufficient to cross-link available proteins so that the bone material comprising the prosthesis is stabilized, strengthened and rendered biocompatible and non-antigenic. This tanning step may be done at any point during preparation of the prosthesis of the invention. Tanning is accomplished by treating the prosthesis with a tanning reagent under tanning conditions until it is strengthened and rendered stable, biocompatible, and non-antigenic. Several tanning procedures are known, and glutaraldehyde is the preferred tanning agent in the method of this invention. The prosthesis is contacted with a buffered solution comprising glutaraldehyde in a concentration sufficient to cross-link available proteins, and the tanning should be done at a physiological pH. Preferably, the prosthesis is submerged in a solution comprising about 0.2% to 0.8% (most preferably about 0.6% (w/v)) glutaraldehyde in a suitable buffer such as HEPES at a pH of 6.8 to 7.5.

The tanning process is continued until proteins are cross-linked to the desired degree (see above). The process may be monitored by any suitable method, including a colorimetric assay using, for example, a ninhydrin reaction (a colorimetric assay for amino groups in which the color intensity decreases as the degree of cross-linking increases.) Advantageously, the prosthesis is treated with glutaraldehyde for one month or more.

Further sterilization of the prosthesis may be accomplished by any suitable means, including but not limited to treatment with ethanol, radiation, or a bacteriocidal solution. Most preferably, a buffered surfactant/formaldehyde/ethanol sterilant is used, as described in co-pending application with Ser. No. 669,735, filed Nov. 8, 1984.

The prostheses can be stored in a suitable sterile solution, preferably 0.05% glutaraldehyde in HEPES buffer, in sterile containers, until needed. The prostheses must be rinsed (e.g., with normal saline) to reduce glutaraldehyde levels (measured by HPLC) to a nontoxic level before implantation. Standard surgical techniques are used to implant the prostheses at the desired location and to cover them with host skin. The implants may be sutured or wired in place, or held in place by host skin. They may be implanted to augment existing tissues or to replace body parts (or portions thereof) which are either missing or which are damaged to some degree by disease or injury. In the latter case, the damaged tissue may be removed surgically before the prosthesis is implanted.

Alternative methods of processing the glutaraldehyde-tanned bone material are within the scope of this invention. For example, bone processed according to the method of the invention can be pulverized or powdered rather than being machined into a desired final shape. Known methods of milling, grinding, and pulverizing can be used to produce pulverized bone with the desired particle size. The pulverized bone can then be combined with any suitable biologically compatible or inert carrier substance. The carrier may be gelatinous substance (biological or non-biological in nature) or a semi-solidified, moldable carrier. The carrier should have a consistency that imparts the desired flexible texture to the pulverized bone/carrier suspension, or should solidify to the desired consistency after molding or casting. Suitable carriers may include but are not limited to gelatins and polysaccharides.

The method of the present invention imparts many desirable properties to the prostheses produced according to it. For example, glutaraldehyde tanning of the bone yields a non-antigenic, biocompatible, and stabilized material, as stated previously. The non-antigenicity allows a prosthesis to be implanted in a host other than the one from which the stock bone was taken to produce the prosthesis.

Glutaraldehyde-tanned bone has been found to have excellent biocompatibility. When glutaraldehyde-treated non-demineralized bone is implanted in host bone in mammals, there is generally no fibrous encapsulation, interposition of fibrous tissue between host bone and implanted bone, or other evidence of host rejection. Instead, the host bone grows into the adjacent implanted bone. This process of host bone ingrowth is termed osteoconduction or osteoinvasion.

Glutaraldehyde tanned and demineralized bone has also been implanted in host bone in mammals, and the material remained soft and again demonstrated good biocompatibility. By contrast, interposition of fibrous tissue and encapsulation are known to be a problem when implants made of less biocompatible materials are introduced into mammals.

One problem associated with prosthesis use is degeneration of the prosthesis, which necessitates frequent replacement. The degenerating material may also migrate and cause problems such as inflammation reactions in the host. The long-term stability imparted to the prostheses of the present invention by glutaraldehyde tanning will solve such problems.

In addition, resorption of implanted bone-derived material is known to occur. The resorbed material may or may not be replaced by the host. In some cases, it may be desirable to implant a prostheses that is resorbed as host tissue replaces it. In such a case, the glutaraldehyde tanning step could be replaced by tanning with different agents (e.g. formaldehyde or alcohols) that would render the bone material resorbable. In most cases, however, it is desirable that the implanted prostheses or template retain its shape and not be resorbed. The cross-linking that occurs during glutaraldehyde treatment produces a stabilized collagen matrix in prostheses produced according to the method of the invention, and the prostheses is generally not resorbed.

The prostheses are derived from a material that is not only biocompatible but hard enough to be shaped, by standard machining techniques, to virtually any desired specifications. The machined bone retains its shape, even for so detailed a pattern as an ear prosthesis, throughout the remainder of the processing. Thus, the demineralized bone retains the desired shape even after it has been rendered flexible and "spongy" in texture.

The method of producing a prosthesis of the present invention is illustrated by the following example. One skilled in the art will recognize the variations in order of steps, prosthesis shape, and other aspects of the method of the invention and the prostheses so produced, which are within the scope of the invention. Thus, the example is meant to illustrate, but not limit, the invention.

EXAMPLE I

Production of Ear Prosthesis

Bone plates were cut from fresh deskinned and dehooved bovine hind legs provided by an abattoir. The bone plate was cut anterior to the ankle-tibia joint, in the region of the epiphyseal plate extending anteriorly approximately 1½ to 2 inches. A thin section of anterior region bone, approximately 3/16 to ¼ inch thick was cut off using a band saw. The section was devoid of all fat and marrow areas. During the sawing and machining steps, the bone piece was frequently bathed in distilled water or saline. A rough outline of the shape of the ear was drawn on the cut plate and this outer circumference geometry was cut from the plate.

Additional guide markings for cavities were made to simulate the shape of natural ear cartilage. A ¼ inch hole was drilled in the bone piece for the opening of the ear canal, and this hole was tapered using a taper bit. ¼-inch drill bit was used to crudely shape cavities, following the guide markings above. The cavities were then opened and smoothed and the final desired contours achieved using a small high-speed hand held drill and a pointed (tapered) grinder.

The finished implant was next demineralized by submersion in 0.6N HCl until completely demineralized, which generally takes about 24 hours. The process was stopped when the implant had the desired degree of flexibility, as determined by feel. At this point, the implant was very flexible and similar in texture to natural ear cartilage. It was also fragile and needed to be handled carefully. The implant was removed from the demineralizing solution and rinsed in buffered normal saline.

The shaped bone piece was then surface cleaned with 100% ethanol to remove machine oils and debris. The bone was submerged in several changes of 100% ethanol for 1-2 hours. The ethanol was kept at approximately 25° C. The alcohol was poured off and the bone piece was rinsed in 0.9% normal saline. Initially, a quick rinse was used to clean the exterior of the bone piece and container, followed by two 30-minute rinses in the saline.

Tanning was accomplished by submerging the prosthesis in 0.625% (w/v) glutaraldehyde in HEPES buffer (pH 6.8 to 7.5) for a minimum of one month. The tanning improved the physical (structural) strength of the prosthesis.

The prosthesis is then sterilized by submersion in a HEPES-buffered solution comprising 4% formaldehyde, 22.5% ethanol, and 1.2% Tween (pH 7.4) for a minimum of eight hours and a maximum of 24 hours at 37° C. The prosthesis is then rinsed (four 10-minute rinses and one 6-hour rinse) and stored (in a sterile container) in 0.05% HEPES-buffered glutaraldehyde until needed for surgical implantation.

Before surgical implantation, the prosthesis will be rinsed with normal saline until residual glutaraldehyde levels (measurable by HPLC) have decreased to a non-toxic level.

The prosthesis produced by these procedures had a detailed shape and contours that closely approximated a human ear. Once surgically implanted and covered with skin, the outer ear area will appear much like a natural human ear.

I claim:

1. A method of producing a flexible, biocompatible, and non-antigenic prosthesis of a precise, intricate shape, for the replacement of a cartilaginous body part, the method comprising:
   a) machining a bone segment into a desired precise, intricate shape which substantially corresponds to the shape of the cartilaginous body part which the prosthesis is to replace,
   b) selectively demineralizing said bone segment to achieve the desired degree of flexibility,
   c) tanning said bone segment.

2. The method of claim 1 wherein the bone segment is tanned with glutaraldehyde.

3. The method of claim 1 additionally comprising extracting the bone segment with an organic solvent to increase the matrix porosity.

4. The method of claims 1 or 3 additionally comprising treating the bone segment with a protease to increase the matrix porosity.

5. The method of claims 1, 2, or 3 additionally comprising sterilizing the prosthesis.

6. The method of claim 2, wherein the bone segment is treated with glutaraldehyde under tanning conditions effective in cross-linking available proteins to a degree sufficient to stabilize and strengthen the bone and to render it biocompatible and non-antigenic.

7. The method of claim 6 wherein tanning is accomplished by submerging the bone segment in a buffered solution comprising 0.2% to 0.8% (w/v) glutaraldehyde.

8. The method of claim 7 wherein the bone segment is submerged in a buffered solution comprising about 0.6% (w/v) glutaraldehyde.

9. The method of claims 6, 7 or 8 wherein the bone is tanned with glutaraldehyde for a minimum of about one month.

10. The method of claim 1 wherein the bone segment is derived from the condylar region of an allogenic or xenogenic long bone.

11. The method of claim 1 wherein demineralizing the bone segment is accomplished by submersion in a solution comprising an acid.

12. The method of claim 11 wherein the acid is HCl.

13. The method of claim 11 wherein said solution additionally comprises up to 1% EDTA.

14. The method of claim 1 additionally comprising submerging the bone segment in ethanol to defat it and to remove machine oils and debris.

15. A prosthesis produced by the method of claim 1.

16. The method of claim 1, wherein, in step (a) the bone segment is machined to the shape of a natural outer ear.

17. The method of claim 1, wherein, in step (a), the bone segment is machined to the shape of a natural chin augmentation implant.

18. The method of claim 1, wherein, in step (a), the bone segment is machined to the shape of a natural nose tip.

19. The method of claim 1, wherein, in step (a) the bone segment is machined to the shape of a natural spinal disc.

20. A prosthesis produced by the method of claim 16.

21. A prosthesis produced by the method of claim 17.

22. A prosthesis produced by the method of claim 18.

23. A prosthesis produced by the method of claim 19.

* * * * *